(12) United States Patent
Iwasaki et al.

(10) Patent No.: US 11,472,945 B2
(45) Date of Patent: Oct. 18, 2022

(54) SLIDABLE RUBBER MATERIAL HAVING AN AMINO-MODIFIED INTERFACIAL MODIFICATION LAYER, AND METHOD FOR PRODUCING SAID SLIDABLE RUBBER MATERIAL

(71) Applicants: ASAHI RUBBER INC., Saitama (JP); ICHINEN CHEMICALS CO., LTD., Tokyo (JP)

(72) Inventors: Kosho Iwasaki, Saitama (JP); Yuko Takami, Saitama (JP); Akira Yoshida, Saitama (JP); Tomoya Uchida, Tokyo (JP); Daisuke Tanaka, Tokyo (JP)

(73) Assignees: ASAHI RUBBER INC., Saitama (JP); ICHINEN CHEMICALS CO., LTD., Tokyo (JP)

(*) Notice: Subject to any disclaimer, the term of this patent is extended or adjusted under 35 U.S.C. 154(b) by 0 days.

(21) Appl. No.: 17/633,984

(22) PCT Filed: Sep. 25, 2020

(86) PCT No.: PCT/JP2020/036380
§ 371 (c)(1),
(2) Date: Feb. 9, 2022

(87) PCT Pub. No.: WO2021/065739
PCT Pub. Date: Apr. 8, 2021

(65) Prior Publication Data
US 2022/0267572 A1    Aug. 25, 2022

(30) Foreign Application Priority Data

Sep. 30, 2019 (JP) .............................. JP2019-180639

(51) Int. Cl.
*C08K 13/02* (2006.01)
*C08L 15/02* (2006.01)
*A61M 5/31* (2006.01)

(52) U.S. Cl.
CPC .............. *C08K 13/02* (2013.01); *C08L 15/02* (2013.01); *A61M 5/3129* (2013.01); *A61M 2005/3131* (2013.01)

(58) Field of Classification Search
CPC ...... C08K 13/02; C09L 15/02; A61M 5/3129; A61M 2005/3131
See application file for complete search history.

(56) References Cited

U.S. PATENT DOCUMENTS

| | | | |
|---|---|---|---|
| 2011/0171480 | A1 | 7/2011 | Mori et al. |
| 2013/0030380 | A1 | 1/2013 | Abe et al. |
| 2014/0319778 | A1 | 10/2014 | Kawasaki et al. |
| 2019/0022986 | A1 | 1/2019 | Nemoto et al. |

FOREIGN PATENT DOCUMENTS

| | | |
|---|---|---|
| JP | 2001323088 A | 11/2001 |
| JP | 2010064667 A | 3/2010 |
| JP | 2010280911 A | 12/2010 |
| JP | 2011148263 A | 8/2011 |
| JP | 2014213092 A | 11/2014 |
| JP | 2017122506 A1 | 11/2018 |
| WO | 2011122574 A1 | 10/2011 |

OTHER PUBLICATIONS

Dec. 1, 2020 International Search Report issued in International Patent Application No. PCT/JP2020/36380.

*Primary Examiner* — Edward J Cain
(74) *Attorney, Agent, or Firm* — Oliff PLC

(57) ABSTRACT

A slidable rubber material that has an amino-modified interfacial layer that does not affect the compression set. Although the slidable rubber material includes a rubber component such as a butyl rubber or halogenated butyl rubber etc. having the low-compression set, which contains a vulcanization agent such as a nitrogen/sulfur compound or a vulcanizing auxiliary agent, the rubber part is coated with a silicone rubber layer. The slidable rubber material exhibits a slidability and resists the detachment or elution of fine particles from the coating layer. A rubber component and a vulcanization agent; an interfacial modification layer that coats the rubber part and an amino-modified silicone compound is incorporated with surface molecules of the rubber part; and a layer that coats the interfacial modification and contains solid fine particles, an addition-type or condensation-type silicone rubber in which the particles are dispersed, and a curing catalyst for silicone rubber.

15 Claims, No Drawings

SLIDABLE RUBBER MATERIAL HAVING AN AMINO-MODIFIED INTERFACIAL MODIFICATION LAYER, AND METHOD FOR PRODUCING SAID SLIDABLE RUBBER MATERIAL

TECHNICAL FIELD

The present invention relates to a slidable rubber material having an amino-modified interfacial modification layer which expresses excellent slidable properties without silicone oil on its exposed surface, and a method for producing the slidable rubber material.

BACKGROUND ART

Syringes which inject a liquid medicine into patients after inhaling it and then pushing it out, pre-filled syringes which inject a pre-sealed liquid medicine into patients or into an infusion solution by pushing it out when used, and syringes for blood drawing are all equipped with an inserted gasket which is installed at the tip of a plunger inside of their syringe cylinders or injectors. These gaskets are required to possess the following features: no leaking between the cylinder of the syringe or injector and the gaskets when the liquid medicine or the blood is inhaled and drained, maintaining liquid sealing without creating gaps and with stable slidability.

To reduce friction and to improve slidability, a silicone oil was previously applied to slidable rubber parts including the above gaskets. For example, Patent Document 1 discloses that a syringe comprises a barrel made of a resin, a gasket that is slidably inserted into the barrel, a plunger installed in the gasket, and a silicone membrane coated with a silicone oil with a kinematic viscosity of 500-100,000 cSt relative to the inner circumference of the barrel and with a coating weight of 5-50 μg per 1 $cm^2$ area.

In recent years, medicines such as a highly functionalized protein medicine or a medicine that controls aggregation of active ingredients have been developed, produced, and sold. When these medicines were injected to patients with a syringe or pre-filled syringe coated with a silicone oil on its gasket, there were several risks, e.g., aggregation of active ingredients including protein through the core of silicone oil droplets, medicine's decreased efficacy or loss and induction of thrombus. And it was not easy to avoid the contamination of the silicone oil in blood samples. In addition, the application of the silicone oil is being avoided from the following viewpoints: minimization of the effects of impurities on the human body and elimination of any factor of affecting measurement reliability as much as possible, because the testing items of blood sample have been increased and there has been some possibility of contamination of impurities with improved detection sensitivity.

Based on these backgrounds, in recent years it is eager to find silicone oil-less syringes and injectors. For example, Patent Document 2 discloses a pre-filled injector gasket, which can seal an inside of a cylinder filled with a liquid medicine and can be slid inside of a cylinder, comprising an elastic gasket body and a laminate layer consisting of a fluoro-resin that covers the surface of the gasket body. Unfortunately, however, the fluoro-resin such as polytetrafluoroethylene (PTFE) is not only quite expensive but also is liable to cause leakage of the liquid between the gasket and the cylinder of syringe or injector as a result of wrinkles caused by friction of a laminate layer during the sliding motion.

In addition, Patent Document 3 discloses a medical equipment owned by a slidable coating layer, which is capable to move in touch with an inner surface of medical rubber parts such as a butyl rubber and polychloroprene rubber or an abdominal cavity, comprising a slidable coating layer provided on a part for touching the inner surface of medical rubber parts or abdominal cavity, wherein the slidable coating layer is formed by a composition containing no solid fine particles and silicone-based resins which is the adduct of silicone with vinyl groups and silicone with hydroxyl groups bound to silicon atoms.

Generally, there have been some problems for the substrates such as a butyl rubber and a halogenated butyl rubber as follows: nitrogen- or sulfur-containing compounds have been used as a vulcanizing agent, and, although an addition-type silicone has been prepared by using a platinum catalyst as a curing catalyst, it was difficult to cause curing when applying to the substrates such as the butyl rubber, because the nitrogen- or sulfur-containing compounds acted as a catalyst poison and caused a catalytic inhibitory effect.

Because of a low permanent compression set of a butyl rubber and a halogenated butyl rubber and also their great utility as raw materials for a variety of slidable medical rubber materials, it is eager to explore their utility as rubber parts, to apply addition-type or condensation-type silicone rubbers without inhibiting the action of a curing catalyst such as platinum catalyst, and to develop new slidable rubber materials with improved sliding characteristics that make it difficult to cause detachment or elution while containing solid fine particles in those silicone rubbers without a silicone oil on the exposed surface thereof.

PRIOR ART DOCUMENT

Patent Document

[Patent Document 1] WO2010/064667
[Patent Document 2] JP2014-213092A
[Patent Document 3] WO2011/122574

SUMMARY OF INVENTION

Problem to be Solved by the Invention

The present invention is made to solve the above problems, and its object is to provide a new slidable rubber material and the method for producing it. Thus, although the slidable rubber material comprises a rubber part made of a rubber component such as a butyl rubber or halogenated butyl rubber etc. having a low permanent compression set, the rubber part is tightly coated with a coating layer containing a silicone rubber without inhibiting curing even with vulcanization agents such as nitrogen/sulfur compounds. This material exhibits excellent slidable properties even though silicone oil is not exposed to the surface, resists detachment and elution of fine particles from the coating layer, and does not affect the basic physical properties such as a permanent compression set.

Means to Solve the Above Problems

A slidable rubber material of the present invention developed to achieve the objects described above, which has an amino-modified interfacial modification layer, comprises:

a rubber part containing a rubber component selected from the group consisting of butyl rubber, halogenated butyl rubber and polychloroprene rubber, a filler, a vulcanization agent and a vulcanizing auxiliary agent; an interfacial modification layer which coats the rubber part and in which an amino-modified silicone compound is incorporated and/or reacted with surface molecules of the rubber part; and a coating layer which coats the interfacial modification layer and contains solid fine particles, an addition-type and/or condensation-type silicone rubber in which the solid fine particles are dispersed, and a curing catalyst for the silicone rubber.

In the slidable rubber material, the amino-modified silicone compound is preferably an amino-modified silicone oil having an amino-substituent on any one of silicone-repeating-units and/or at a terminal; or an amino-modified silicone oil having an amino-substituent on any one of silicone-repeating-units and/or at a terminal while having a hydroxyl group or a protected hydroxyl group on any one of silicone-repeating-units and/or at a terminal.

In the slidable rubber material, the solid fine particles are silica fine particles and/or silicone particles.

In the slidable rubber material, a thickness of the coating layer is preferably 5-30 µm.

In the slidable rubber material, an average particle size of the solid fine particle may be 0.1-10 µm.

In the slidable rubber material, it is preferable that a part of the solid fine particle provides with an uneven surface on the coating layer.

In the slidable rubber material, it is preferable that the coating layer neither include nor hold a silicone oil inside and on an exposed surface thereof In the slidable rubber material, the filler is silica, talc, titanium oxide, carbon black, clay, and/or calcium carbonate.

In the slidable rubber material, the vulcanizing agent is a mercaptobenzimidazole derivative and/or a triazine dithiol derivative.

In the slidable rubber material, the vulcanizing auxiliary agent is an organic acid zinc salt.

In the slidable rubber material, the rubber part includes any one selected from the group consisting of an acid-acceptor selected from magnesium oxide, zinc oxide, and natural or synthetic hydrotalcite, an alkoxysilane compound, and a softening agent selected from an organic resin, and a silicone oil or a paraffin oil.

In the slidable rubber material, the curing catalyst is a platinum catalyst.

In the slidable rubber material, the coating layer may be provided over the interfacial modification layer directly or through a primer layer.

The slidable rubber material is used for medical purposes.

The slidable rubber material can be used for a gasket of a syringe or of an injector.

A method for producing the above slidable rubber material, which has an amino-modified interfacial modification layer, comprises: forming an interfacial modification layer by applying a composition containing an amino-modified silicone compound for forming the interfacial modification layer onto a rubber part containing a rubber component selected from the group consisting of butyl rubber, halogenated butyl rubber and polychloroprene rubber, a filler, a vulcanization agent and a vulcanizing auxiliary agent, and then, covering the interfacial modification layer through a coating layer by applying a composition containing solid fine particles, an addition-type and/or condensation-type silicone rubber ingredients in which the solid fine particles are dispersed, and a curing catalyst for the silicone rubber.

Effects of the Invention

The slidable rubber material containing the amino-modified interfacial modification layer of the present invention provides with the following features: the rubber part made of the rubber component such as the butyl rubber or halogenated butyl rubber, etc. having a low permanent compression set and excellent elasticity. And, although the rubber part contains the vulcanization agent such as a nitrogen/sulfur compound or zinc compound, the rubber part is tightly coated with the coating layer containing the addition-type and/or condensation-type silicone rubber without inhibiting the curing due to the presence of the interfacial modification layer having the amino-modified silicone compounds. Furthermore, the amino-modified silicone compounds incorporated in the interfacial modification layer can make a bond with the surface molecules of the rubber parts, can contain the vulcanization agent such as the nitrogen/sulfur compound, or the like, and also can make a strong tight seal of the coating layer through the significant interaction with the components of the coating layer. The slidable rubber material can make it possible to make a good seal to the coating layer by the formation of the interfacial modification layer on the rubber part substrates, and hence can express sufficient slidability and durability.

The above slidable rubber material expresses excellent slidability, because the solid fine particles, not silicone oil, is contained in the coating layer and/or partially exposed from it. In addition, due to the difficulty to cause detachment and elution of those solid fine particles, the material is low-dusting and suitable for medical use.

The above slidable rubber material exhibits high liquid-sealing properties due to the excellent physical property of the rubber part made of the rubber component with sufficient elasticity such as the butyl rubber or halogenated butyl rubber.

The above slidable rubber material is useful as a slidable material for various applications such as the gasket for medical syringes or injectors that requires sufficient slidability and liquid-sealing ability without affecting basic properties such as a low permanent compression set inherent in the rubber part made of the rubber component such as the butyl rubber or halogenated butyl rubber.

Since the slidable rubber material is excellent in fluidity and moldability of the composition used for forming the rubber component, a large amount of filler can be added without lowering the productivity. Further, the slidable rubber material has high storage stability, preservation of properties and performance, and is molded with a composition for rubber parts having excellent moldability so that the defect rate, which is the ratio of defective products to the number of products produced, is low and high productivity can be kept.

In the above slidable rubber material, the interfacial modification layer and a coating layer are arranged successively on a rubber part made of a rubber component with sufficient elasticity. And because of their strong bond strength, it can follow elasticity and slidability, and does not cause detachment and elimination.

The above slidable rubber material is strictly contained by the coating layer even if the interfacial modification layer contains the amino-modified silicone compounds such as the amino-modified silicone oil, and hence it does not cause elution of the amino-modified silicone compounds.

The above slidable rubber material can avoid to cause the aggregation of active ingredients that must be derived from the contamination of a silicone oil as a core, which has been conveniently used to gain slidability, because the coating layer does not contain and hold silicone oil both inside and on an exposed surface thereof. In addition, since it is difficult to detach and to elute the solid fine particles from the coating layer, it can improve safety and reliability. In conclusion, even if a highly functionalized protein medicine, a suitably controlled medicine protected from the aggregation of active ingredients or a medicine to avoid contamination was inhaled into the syringe or inserted into the pre-filled syringe, it is possible to suppress the aggregation of active ingredients and detachment and elution of impure alien substrates, it can be maintained for a long time with high-quality, it does not reduce medicine's efficacy or cause it to be lost when used, and finally it does not induce side effects such as thrombus.

Even if the above slidable rubber material was used as the gasket of syringe for blood test, it is difficult to cause detachment and elution of silicone oil, filler and solid fine particles and hence it does not cause contamination of impure alien substrates in blood test samples. In addition, although the testing items of blood samples are increased and the detection sensitivity is improved, there is no risk of affecting on the reliability of the measurement results, and accurate and precise medical tests can be performed.

The above slidable rubber material can fulfill the standard set at The Japanese Pharmacopoeia such as the standard test for a rubber stopper used for liquid transfusion. And based on the facts that eluates to contact liquids such as water or medical solution are extremely low and the generation of chlorides as the set for a water purity test is suppressed, thereby the slidable rubber material can be used as the gasket for medical syringe or injector.

And, the above slidable rubber material can suppress the generation of distortion during sterilization from room temperature to heating. In particular, when heating or cooling is applied under pressure such as sterilization, it is surely difficult to cause a re-vulcanizing reaction such as a recombination between the vulcanization agent and the products formed by a scission of vulcanized chains with heating. As a result permanent compression set due to the decrease in recovery stress caused by the change in internal structure due to the scission of vulcanized chains and re-changing is greatly reduced. By suppressing the permanent compression set, the degree of sealing and resistance changes are minimal and the excellent liquid sealing performance can be maintained.

According to the producing method for the slidable rubber material of the present invention, the slidable rubber material having the above characteristics can be easily produced by a simple operation in high quality, high volume and good yield rate.

According to the above method, since it can be manufactured with inexpensive raw materials, it can contribute to the reduction of medical expenses. Furthermore, since it can be stored at the stage where the interface modification layer has been established, it is possible to easily manufacture a variety of the slidable rubber materials by changing the coating layer's type as appropriate.

Embodiments to Implement the Invention

The following details embodiments for implementing the present invention, but the scope of the present invention is not limited to these embodiments.

In the present invention, a slidable rubber material containing an amino-modified interfacial modification layer contains the following features: a rubber part containing a rubber component selected from a butyl rubber, halogenated butyl rubber and polychloroprene rubber, a filler and a vulcanization agent; an interfacial modification layer that is provided on the rubber part by being applied to cover it and contains amino-modified silicone compounds; and a coating layer that is provided on the interfacial modification layer to cover this and also contains solid fine particles, a silicone rubber and a curing catalyst thereof.

The above slidable rubber material contains the vulcanization agent as a catalyst poison that inhibits curing of the coating layer containing an addition-type and/or a condensation-type silicone rubber, but the vulcanization agent can be sealed so as not to prevent adverse effects, because the rubber part is coated by the interfacial modification layer containing amino-modified silicone compounds. Thus, even if the coating layer, which covers the interfacial modification layer and contains solid fine particles, a silicone rubber and a curing catalyst, is over-coated on the interfacial modification layer, the curing catalyst is not affected by the vulcanization agent. The silicone rubber is sufficiently cured for strength and flexibility and can form the coating layer that can be followed.

As materials of the rubber part, the rubber component is selected from the groups consisting of a butyl rubber such as a copolymer rubber of isobutylene and isoprene, a halogenated butyl rubber such as a chlorinated butyl rubber, a brominated butyl rubber, a polychloroprene rubber, a copolymer of chlorinated isobutylene and isoprene, a copolymer of brominated isobutylene and isoprene, and a bromine-added copolymer of isobutylene and p-methylstyrene. These rubber components can be used as a raw material of the slidable rubber, in particular, the slidable rubber for medical use that needs to reduce the permanent compression set.

The filler may be granules or a powder, also white or colored colorants, and is exemplified with an inorganic filler such as talc, silica, titanium oxide, carbon black, clay, and calcium carbonate.

As the filler, for example, the silica can be obtained by a precipitation method. This may possess an average particle diameter of 30 μm and, for example, this may be a large-sized silica having an average particle diameter of 15-60 μm by Laser diffraction particle distribution measurement. Specifically, this may be Nipsil EL, Nipsil ER, Nipsil VN3 and Nipsil AQ (all trade names, available from Tosoh Silica Corporation).

As a filler, it is favorable that talc has a calcium content of less than 0.9% detected by the talc purity test at The Japanese Pharmacopoeia Seventeenth Edition, and more favorably a calcium content is less than 0.1%. The talc powder as the filler is manufactured by grinding a raw stone of talc which occurs as a natural mineral, and hence their associated minerals must be contained as impurities. Among these impurities, calcium-containing dolomite ($CaMg(CO_3)_2$) or calcite ($CaCO_3$) is basic when placed in water, and therefore it is liable to affect the ApH values and adversely to affect elution characteristics in the eluate test due to much content thereof. Specifically, the favorable talc may be GH3 (trade name, available from Hayashi Kasei Co., Ltd.), MMR (trade name, available from Asada Milling Co., Ltd.), GATH40 (trade name, available from Nippon Talc Co., Ltd.), and Victory Light SK-C (trade name, available from Shokozan Mining Co., Ltd.).

As the filler, titanium oxide may be a rutile-type or an anatase-type, and manufactured by a chlorine method or a sulfuric acid method, favorably by a sulfuric acid method. Specifically, this may be Tipaque (trade name, available from Ishihara Sangyo Kaisha, Ltd.), TR-600 (trade name, available from Fuji Titanium Industry Co., Ltd.), and JR-405 (trade name, available from Tayca Corporation).

As the filler, carbon black may be manufactured by any one of an oil furnace method, an acetylene decomposition method, a thermal method, a contact method, and the like, and its particle diameter is favorably 30-350 nm. Specifically, this may be Asahi Thermal, Asahi #15, Asahi #15HS, Asahi #35, Asahi #50, Asahi #50U, Asahi #51, Asahi #55 and Asahi #60U (all trade names, available from Asahi Carbon Co., Ltd.), HTC #20, HTC #SL, HTC #S, Niteron #SH, Niteron #55S, HTC #100, Niteron #10S, Niteron #10K, Niteron #10, Niteron #200IN and Niteron #200L (all trade names, available from Nippon Steel Carbon Co., Ltd.), and Seast TA, Seast SP, Seast S, Seast FY, Seast SVH, Seast V, Seast SO, Seast 116 and Seast 116HM (all trade names, available from Tokai Carbon Co., Ltd.).

As the filler, clay can be a wet-type clay or a firing clay, and its particle diameter is favorably 5-100 μm. Specifically, this may be Catalpo and OA Clay (trade name, available from Sanyou Clay Industry Co., Ltd.), Satintone W and Satintone No. 5 (trade names, available from BASF Ltd.), and Glomax LL, Glomax LX, PoleStar 400, PoleStar 200R and Metastar 501 (all trade names, available from Imerys Minerals Japan Co., Ltd.).

As the filler, calcium carbonate may be natural calcium carbonate, minor calcium carbonate, ground calcium carbonate, colloidal calcium carbonate, basic calcium carbonate and surface-treated calcium carbonate. Specifically, this may be Hakuenka CC, Hakuenka U, Hakuenka CCR, Vigot 10, Vigot 115, Hakuenka O, Hakuenka DD, Calmos, Hakuenka AA, Hakuenka A and Brilliant-1500 (all trade names, available from Shiraishi Calcium Kaisha, Ltd.), MSK-C, Kalfain 200, Kalfain 200M, Kalfain 500 and Kalfain N-40 (all trade names, available from Maruo Calcium Co., Ltd.), and Socal 311, Socal 312, Socal 322, Winnofill SPT and Winnofil S (all trade names, available from Imerys Minerals Japan Co., Ltd.).

The above filler may be a packing agent designed to improve mechanical strength and color. These fillers can be used alone or with multiple mixes.

These fillers can be treated with an alkoxysilane compound on its surface. As described below, this alkoxysilane compound may be a silane coupling agent, e.g., an alkoxysilane compound that may be further contained in the composition for rubber parts.

In the rubber part, the filler content is favorably 10-150 parts by mass for the 100 portions by mass of the rubber component, and more favorably 20-150 parts by mass.

The vulcanization agent may be a nitrogen- or sulfur-containing compound. The vulcanization agent is used to vulcanize the composition for rubber parts containing the rubber component, filler and vulcanization agent to form rubber parts.

In the vulcanization agent, a nitrogen- or sulfur-containing compound may be triazinethiol derivatives and 2-mercaptobenzimidazole derivatives. Specifically, the triazinethiol derivatives are shown in Chemical Formula (1):

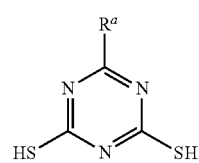

(1)

(in the above Formula (1), symbol $R^a$ denotes —SH, —OR$^1$, —SR$^2$, —NHR$^3$, or —NR$^4$R$^5$ ($R^1$, $R^2$, $R^3$, $R^4$ and $R^5$ may be identical or different respectively, and may be an alkyl group, alkenyl group, allyl group, aralkyl group, alkylallyl group, and cycloalkyl group. $R^4$ and $R^5$ can be identical or different. $R^1$-$R^5$, and may be linear, branched, and/or cyclic with a maximum of 20 carbon atoms));

the 2-mercaptobenzimidazole derivatives are shown in Chemical Formula (2):

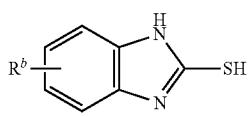

(2)

(in the above Formula (2), symbol $R^b$ denotes a hydrogen or methyl group).

As the vulcanization agent, the triazinedithiol derivatives may be specifically 2-dibutylamino-4,6-dimercapto-s-triazine, 2-anilino-4,6-dimercapto-s-triazine, and 2,4,6-trimercapto-s-triazine.

In the rubber part, the content of the triazinedithiol derivatives is favorably 0.5-2.0 parts by mass for the 100 portions by mass of the rubber component, and more favorably 0.5-1.5 parts by mass. If the content of the triazinedithiol derivatives was less than 0.5 parts by mass, sufficient vulcanization cannot be attained.

As the vulcanization agent, the 2-mercaptobenzimidazole derivatives may be, more specifically, 2-mercaptobenzimidazole and 2-mercapto-5-methylbenzimidazole.

In the rubber part, the content of the 2-mercaptobenzimidazole derivatives is favorably 0.5-1.5 parts by mass for the 100 portions by mass of the rubber component.

As the vulcanization auxiliary agent, a zinc compound may be an organic acid zinc salt. The organic acid zinc salt may be a zinc salt of saturated or unsaturated aliphatic acids with 10-24 carbon atoms, or of aromatic carboxylic acids: specifically, stearic acid zinc salt, behenic acid zinc salt and montanic acid zinc salt. The organic acid zinc salts can regulate the time until the vulcanization reaction starts and the reaction rate of vulcanization, and thereby the vulcanization reaction can be controlled, when the composition for rubber parts is vulcanized.

In the rubber part, the content of the organic acid zinc salt is less than 0.5 parts by mass for the 100 portions by mass of the rubber component. But in order to control the vulcanization reaction, its content is favorably 0.1 parts by mass or more and less than 0.5 parts by mass, and more favorably 0.2-0.3 parts by mass. Even if the content of the organic acid zinc salt is 0.5 parts by mass or more, the effect of extending the start time of the vulcanization reaction in proportion to the amount of additive is not achieved, and it is not desirable because it also increases the amount of zinc elution.

In the slidable rubber material, the rubber part may contain optionally the above components plus additives. The additives may be an acid-acceptor selected from magnesium oxide, zinc oxide and natural or synthetic hydrotalcite; an anti-adhesion and viscosity regulator such as stearic acid, or the like; an organic resin such as polyethylene and aliphatic/aromatic hydrocarbons, and a processing auxiliary agent such as a softener like a silicone oil and paraffin oil. As the acid-acceptor, in order to prevent the elution of zinc and the generation of chlorides, it is preferable to use magnesium oxide with a BET-specific surface area of 30-165 m$^2$/g, which can be determined by a BET (Brunauer-Emmett-Teller) method. The highly productive vulcanization reaction with long start time and short time to reach equilibrium vulcanization can be achieved by blending in particular with medium active magnesium oxide with the BET-specific surface area of 30-40 m$^2$/g, while the eluate and the permanent compression set remain low.

The composition for rubber parts may contain alkoxysilane compounds. These alkoxysilane compounds, for example, can act as a silane coupling agent. These alkoxysilane compounds may be alkoxysilane compounds containing mercapto groups, mercapto-producing functional groups, amino groups and/or amino-producing functional groups. The mercapto-producing or amino-producing functional group is a group that produces an SH— or NH$_2$-group by reduction or deblocking.

One of the examples of the above alkoxysilane compounds may have an alkoxy group, but it also has a mercapto-group and/or mercapto-producing group. The mercapto-producing functional group is a group that produces an SH-forming group by reduction or deblocking. For example, bis(3-(triethoxysilyl)propyl)tetrasulfide (TESPT) does not have an SH group within its structure, but it can generate an —S—SH group or —SH group by the disconnection of some bonds in the middle of the chain of four sulfur atoms connected together (—S—S—S—S—) during vulcanization. Specifically, this may be a polysulfide group (—(S)$_n$—, n=2-4) such as a disulfide function (—S—S—) and protected mercapto-group with a methyl or trimethylsilyl group.

The above alkoxysilane compounds may be an alkoxysilane compound containing an alkoxy- and mercapto-group, typically, 3-mercaptopropyltrimethoxysilane and 3-mercaptopropylmethyldimethoxysilane; as alkoxysilane compounds containing an alkoxy- and mercapto-producing functional group, typically, an alkoxysilane compound containing a polysulfide function or a block body of alkoxysilane compounds containing a mercapto function such as bis(3-(triethoxysilyl)propyl)tetrasulfide. Among these, 3-mercaptopropyltrimethoxysilane is recommended. These alkoxysilane compounds can be used alone or with multiple mixes.

Another example of the above alkoxysilane compounds is an alkoxysilane compound containing an alkoxy group, but also containing an amino group and/or an amino-producing functional group. For example, this may be alkoxysilane compounds containing an amino group or its block body. The amino-producing compound, for example, may contain protected amino groups, e.g., a protected amino group having a carbamate-type protective group such as a tert-butoxycarbonyl or benzyloxycarbonyl group; a protected amino group having amide-type protective group, a protected amino group having an imide-type protective group such as a phthaloyl group; a protected amino group having a sulfonamide-type protective group such as a p-toluenesulfonyl or 2-nitrobenzenesulfonyl group.

The above alkoxysilane compounds may be alkoxysilane compounds containing both an alkoxy group and an amino group, e.g., 3-aminopropyltrimethoxysilane, 3-aminopropyltriethoxysilane, N-2-(aminoethyl)-3-aminopropylmethyldimethoxysilane and N-2-(aminoethyl)-3-aminopropyltrimethoxysilane. Among these, 3-aminopropyltrimethoxysilane is recommended. These alkoxysilane compounds can be used alone or with multiple mixes.

The content of the above alkoxysilane compounds is favorably 0.2-2.0 mass % for the filler mass portion, and more favorably is 0.5-2.0 mass % in the blend of the composition for rubber parts.

These alkoxysilane compounds are connected with the filler surface by combining with the composition for rubber parts and/or providing the surface treatment of the filler, and the filler and polymers are bonded together via the alkoxysilane compounds thereof. In the rubber part, the filler can connect with the main chain of polymers by making bonds with the rubber components such as the halogenated rubbers through the alkoxy silane compounds, to construct a three-dimensional mesh structure.

Specifically, this is a substance in which reactive functional groups of a hydroxyl group on a filler surface react with hydrolyzing groups of an alkoxy group in alkoxysilane compounds to form bonds, and further an amino- or amino-producing group of those alkoxysilane compounds or a mercapto-group or mercapto-producing group such as a disulfide group reacts with halogen atoms of halogenated rubbers to form bonds. The bond between the alkoxysilane compounds and the filler may be spread out over several parts on the filler surface, and the filler surface may be bonded to coat with the alkoxysilane compounds.

In the rubber part, the above filler connects with the polymer chain via the alkoxysilane compounds. As a result of a hydrophobic property of the filler surface connected with the alkoxysilane compounds, it is difficult to extract the permanganate reductants to the contact fluid side even during elution tests in rubber plug testing method for fluids at The Japanese Pharmacopoeia. And it is favorable that these fillers are treated with alkoxysilane compounds on their surface, and hence the permanent compression set can be reduced significantly because of no misalignment of the interface with the halogenated rubbers.

Accordingly, the alkoxysilane compounds are contained with the fillers in forming chemical bonds on their filler surface, and can prevent misalignment of the interface, which is one of the causes of permanent compression set, between the filler and the polymer formed by halogenated rubbers, and this leads to the considerable reduction of the permanent compression set. In addition, the alkoxysilane compounds can prevent metal oxides such as magnesium oxide and zinc oxide as the composition for rubber parts from forming metal chlorides such as magnesium chloride and zinc chloride and from eluting from the rubber parts.

The interfacial modification layer, in which the amino-modified silicone compounds are contained and/or are reacted with the rubber component, typically the halogenated butyl rubber of the rubber part at least in a part thereof, covers the rubber part. Because the rubber component such as the butyl rubber and halogenated butyl rubber of the rubber parts ensures a strong bond formation, especially a halogen atom of the halogenated butyl rubber and an amino group of the amino-modified silicone compounds ensure the strong bond formation by at least the partial substitution reaction of them, the vulcanization agent is contained in the rubber parts. Such interfacial modification layer may be a single-molecule layer with many molecules of amino-modified silicone compounds or may be a layer where many molecules of amino-modified silicone compounds bind and are cured.

The above amino-modified silicone compounds that form the interfacial modification layer may be an amino-modified silicone oil introduced with an organic group including an amino-group. For example, this may be an amino-modified silicone oil with an amino-group on any one of the silicone repetitive units and/or at the terminal or the amino-modified silicone oil with an amino-group on one of the silicone repetitive units and/or at the terminal plus a hydroxyl- or protected hydroxyl-group on any one of the silicone repetitive units. As amino-substituents, an amino-group, an aminopropyl-group and an N-(β-aminoethyl)iminopropyl-group are exemplified and a mono-amino-substitution or a polyamino-substitution such as a diamino-substitution is also acceptable.

The above interfacial modification layer can be prepared by immersing the optionally-cleaned rubber parts to the composition for interfacial modification layers consisting of emulsion containing the amino-modified silicone compounds, water rinsing and drying as appropriate. In this case, an amino-substituent or a hydroxyl-group of amino-modified silicone compounds reacts with a halogen-group of the rubber components such as the halogenated butyl rubber of the rubber parts and with a surface hydroxyl-group of the fillers such as the silica and talc to form covalent bonds and membrane-like interfacial modification layers. The formation of those interfacial modification layers leads to the modification of the rubber parts containing the rubber component such as the butyl rubber or halogenated butyl rubber, etc. The amino-modified silicone compounds are designed to strengthen the interaction with the coating layer attached to the rubber part and ensure a good seal, and is capable of expressing excellent slidability and durability.

The amino-modified silicone oil is exemplified with: $(CH_3)_3SiO-[Si(CH_3)_2-O-]_{x1}-[Si(CH_3)(amino\text{-}substituent)\text{-}O-]_{y1}-Si(CH_3)_3$ (3), $R^c-Si(CH_3)_2-O-[Si(CH_3)_2-O-]_{x2}-[Si(CH_3)(amino\text{-}substituent)\text{-}O-]_{y2}-Si(CH_3)_2-R^c$ (4), $R^c-Si(CH_3)_2-O-[Si(CH_3)_2-O-]_{x2}-[Si(CH_3)(amino\text{-}substituent)\text{-}O-]_{y3}-[Si(amino\text{-}substituent)_2-O-]_{y4}-Si(CH_3)_2-R^c$ (5), or amino-substituent-$[Si(CH_3)_2-O-Si(CH_3)_2-O-]_{x3}-Si(CH_3)_2$-amino-substituent (6) (In the Formulae (3)-(6), symbols x1-x3 and symbols y1-y4 denote each repeating unit numbers wherein those units denote random units and/or block units, and its functional group equivalent is 100-8000. $R^c$ denotes a hydroxyl-, methoxy-, ethoxy-, or propyloxy-group). And this may be a modified silicone oil containing an amino-group on the side chain or at the terminal with a total number of repeating units 5-100.

The amino-modified silicone oil shown by the Formulae (3)-(6), specifically, may be DOWSIL BY16-205 (viscosity 90 mm²/s [25° C.], functional group equivalent 3900), DOWSIL BY16-213FLUID (viscosity 60 mm²/s [25° C.], functional group equivalent 2700), DOWSIL BY16-849FLUID (viscosity 1200 mm²/s [25° C.], functional group equivalent 600), DOWSIL BY16-853U (viscosity 14 mm²/s [25° C.], functional group equivalent 450. Biterminal-type), DOWSIL BY16-871 (viscosity 4 mm²/s [25° C.], functional group equivalent 130. Biterminal-type), DOWSIL BY16-872 (viscosity 18100 mm²/s [25° C.], functional group equivalent 1800), DOWSIL BY16-879B (viscosity 1500 mm²/s [25° C.], functional group equivalent 7500. Biterminal OH-type), DOWSIL BY16-892 (viscosity 1400 mm²/s [25° C.], functional group equivalent 1900. Biterminal OH-type), DOWSIL FZ-3705 (viscosity 250 mm²/s [25° C.], functional group equivalent 3800), DOWSIL FZ-3710 (viscosity 1000 mm²/s [25° C.], functional group equivalent 1750), DOWSIL FZ-3760 (viscosity 220 mm²/s [25° C.], functional group equivalent 1700), DOWSIL FZ-3785 (viscosity 3500 mm²/s [25° C.], functional group equivalent 6000), and DOWSIL SF8417FLUID (viscosity 1200 mm²/s [25° C.], functional group equivalent 1800) (all trade names, available from Dow-Toray Co., Ltd.); KF-857 (viscosity 65 mm²/s [25° C.], functional group equivalent 790. Biterminal methoxy-type), KF-8001 (viscosity 240 mm²/s [25° C.], functional group equivalent 1900. Biterminal methoxy-type), and KF-862 (viscosity 650 mm²/s [25° C.], functional group equivalent 1900. Biterminal methoxy-type) (all trade names, available from Shin-Etsu Chemical Co., Ltd.); TSF4703 (viscosity 1000 m Pa·s [25° C.], functional group equivalent 1600), TSF4704 (viscosity 40000 mPa·s [25° C.], functional group equivalent 20000), TSF4705 (viscosity 70000 mPa·s [25° C.], functional group equivalent 40000), TSF4707 (viscosity 10000 mPa·s [25° C.], functional group equivalent 7000), TSF4708 (viscosity 1000 mPa·s [25° C.], functional group equivalent 2800), XF42-B1989 (viscosity 900 mPa·s [25° C.], functional group equivalent 0.9 Nwt %) and XF42-B8922 (viscosity 70000 mPa·s [25° C.], functional group equivalent 0.1 Nwt %) (all trade names, available from Momentive Performance Materials Japan LLC).

As the above amino-modified silicone oil, in particular, the substance shown by the Formula (4) or (5) is favorable.

In the emulsion containing the amino-modified silicone oil, the concentration of the modified silicone oil is not particularly limited, but, specifically, the favorable concentration is 0.0002-0.5 mass %, and more favorably 0.01-0.3 mass %. This emulsion may contain surfactants. The surfactants include anionic surfactants such as an alkylsulfonic acid salt, alkylbenzenesulfonic acid salt and alkylphosphonic acid salt, etc.; non-ionic surfactants such as a polyoxyalkylene alkyl ether, polyoxyethylene alkylphenyl ether, polyoxyethylene aliphatic acid ester and sorbitan aliphatic acid ester, etc.; cationic surfactants such as a quaternary ammonium salt and alkylamine acetic acid salt, etc., amphoteric surfactants such as an alkylbetaine and alkylimidazoline, etc. The emulsion containing amino-modified silicone compounds may contain dissolving agents, e.g., ethers such as a polyoxyethylene branched alkyl (C12-C14) ether, siloxanes such as octamethylcyclotetrasiloxane, and organic acids such as acetic acid.

The emulsion containing amino-modified silicone compounds may be an emulsion coexisting with surfactants or commercially available. The silicone oil emulsion with a concentration of 20-80 mass % is commercially available. This may be DOWSIL FZ-4658, DOWSIL FZ-4634EX, and DOWSIL SM8709SR Emulsion (all trade names, available from Dow-Toray Co., Ltd.); POLON-14, POLON-MF-14EC, KM-9771, and POLON-MF63 (all trade names, available from Shin-Etsu Chemical Co., Ltd.); or XS65-00032, XS65-00726, XS65-B6413, and XS65-B8124 (all trade names, available from Momentive Performance Materials Japan LLC). The commercial material may be used after dilution to 0.0002-0.5 mass %.

The above interfacial modification layer can suppress contact with the vulcanization agent present in the rubber part and the curing catalyst in the coating layer such as a platinum catalyst by covering the rubber part, and can assist a coating agent to be tightly covered.

The coating layer that is covered with the above interfacial modification layer and yet contains solid fine particles, an addition-type and/or condensation-type silicone rubber that dispersed solid fine particles and a curing catalyst is covered by firm hardening on rubber parts via an interfacial modification layer. In particular, the use of an addition-type silicone rubber is favorable.

In coating layers, the solid fine particles may be a silica fine particle or a silicone fine particle selected from a silicone rubber and a silicone resin, etc. In particular, the silicone fine particle is favorable.

The coating layer is prepared by applying the composition for coating layers, which contains the solid fine particles, the addition-type and/or condensation-type silicone rubber ingredients that disperse the solid fine particles, the curing catalyst, and, if necessary, diluting solvents such as one or more aliphatic solvents, after mixing and blending, to the interfacial modification layer and then heating it to cure it.

The above solid fine particles possess an average particle diameter of 0.01-30 μm and favorably 0.1-10 μm by laser diffraction-type particle distribution measurement. And it is preferable to have a coating layer thickness of 5-50 μm, more favorably 5-30 μm. In this case, an uneven surface is formed on the coating layer by adjusting both the average particle diameter of the solid fine particles and the thickness of the coating layer.

The solid fine particles which form an uneven surface on the coating layer possess the following features. Thus, due to the fact that the above ingredients adhere to the surface of the solid fine particles in the composition for coating layers in which addition-type and/or condensation-type silicone rubber ingredients are mixed and blended, the solid fine particles protruding from the coating layer resist detachment or elution, and the solid fine particles which form the uneven surface reduce the contact area towards an inner wall of a syringe or injector to improve its slidability, and further the elastic nature of the addition-type or condensation-type silicone rubber assists to maintain their liquid-sealing property. In the presence of solid fine particles, the dynamic slidability resistant value of the coating layer falls to about 4-8N. For example, when to a syringe barrel for 1 mL of outer COP-resin barrel (the inside diameter is about φ 6.35 mm), the gasket with the same outside diameter (φ about 6.60-6.75 mm) was subjected to sliding, the dynamic slidability resistant value can be lowered to 10N or less for 100 mm/min.

The hardness of a silicone rubber component in the composition for coating layers is a Duro A hardness of 30-70°, favorably 30° (JIS K 6253 Duro A).

The addition-type silicone rubber ingredient in the coating agents may be a mixture of organopolysiloxanes bearing vinyl functions and hydrogenorganopolysiloxanes, and its component ratio is 0-67 weight %. On the other hand, the condensation-type silicone rubber ingredient is a mixture of organopolysiloxanes bearing silanol functions and organoalkoxysilanes, and its component ratio is 0-67 weight %. The component ratio of the solid fine particles is 0.1-50 weight % as a concentration in the final coating layer, and a diluting solvent such as aromatic, aliphatic, alicyclic, ethers, esters, ketones, and alcohols, etc. is added, if necessary, and its component ratio is 30-99 weight %.

Examples of the organopolysiloxanes bearing vinyl functions are vinylmethylsiloxane/polydimethylsiloxane copolymer, vinyl terminal-polydimethylsiloxane, vinyl-terminal diphenylsiloxane/polydimethylsiloxane copolymer, vinyl terminal-diethylsiloxane/polydimethylsiloxane copolymer, vinyl-terminal trifluoropropylmethylsiloxane/polydimethylsiloxane copolymer, vinyl-terminal polyphenylmethylsiloxane, vinylmethylsiloxane/dimethylsiloxane copolymer, trimethylsiloxane-group terminal dimethylsiloxane/vinylmethylsiloxane/diphenylsiloxane copolymer, trimethylsiloxane-group terminal dimethylsiloxane/vinylmethylsiloxane/bistrifluoropropylmethylsiloxane copolymer, organopolysiloxanes bearing vinyl functions such as trimethylsiloxane-group terminal polyvinylmethylsiloxane, or the like.

Examples of the hydrogenorganopolysiloxanes are organopolysiloxanes bearing hydrogen such as hydrogen terminal polysiloxane, methylhydrogensiloxane/dimethylsiloxane copolymer, polymethylhydrogensiloxane, polyethylhydrogensiloxane, hydrogen terminal polyphenyl (dimethylhydrogensiloxy)siloxane, methylhydrogensiloxane/phenylmethylsiloxane copolymer, methylhydrogensiloxane/octylmethylsiloxane copolymer, or the like.

Examples of the organopolysilanes bearing silanol functions are silanol terminal polydimethylsiloxane, silanol terminal polydiphenylsiloxane, silanol terminal polytrifluoromethylsiloxane, silanol terminal diphenylsiloxane/dimethylsiloxane copolymer, or the like.

Examples of the organoalkoxysilanes are tetraethoxysilane, methyltrimethoxysilane, vinyltrimethoxysilane, methyltriethoxysilane, vinyltriethoxysilane, ethyl orthosilicate, propyl orthosilicate, aminopropyltriethoxysilane, or the like.

Examples of the catalysts to carry out the addition reaction (i.e., hydrosilylation) of the organopolysiloxanes bearing vinyl functions with the hydrogenorganopolysiloxanes are platinum, platinum compounds, palladium compounds, rhodium compounds, or the like, and among them, in particular, platinum and platinum compounds are favorable. The catalytic use of this catalyst is enough, and its platinum amount conversion is usually adjusted to 1-1000 ppm for the organosiloxanes bearing vinyl functions.

Examples of the catalysts to carry out the condensation reaction of the organopolysiloxanes bearing silanol functions with organoalkoxysiloxanes are carboxylic acid metal salts, organotin compounds, alkoxytitanium compounds, organoaluminum compounds, organozirconium compounds, or the like.

The composition for coating layers may be commercially available. For example, this may be SILASTIC RBL-9200-30 Liquid Silicone Rubber, SILASTIC RBL-9200-40 Liquid Silicone Rubber, SILASTIC RBL-9200-50 Liquid Silicone Rubber, SILASTIC RBL-9200-60 Liquid Silicone Rubber, and SILASTIC RBL-9200-70 Liquid Silicone Rubber (all trade names, available from Dow-Toray Co., Ltd.); KE-1950-30-A/B, KE-1950-40-A/B, KE-1950-50-A/B, KE-1950-60-A/B, KE-1950-70-A/B, KEG-2000-30-A/B, KEG-2000-40-A/B, KEG-2000-50-A/B, KEG-2000-60-A/B, KEG-2000-70-A/B, KEG-2001-40-A/B, KEG-2001-50-A/B, and KEG-2001-60-A/B, KEG-2001-70-A/B (all trade names, available from Shin-Etsu Chemical Co., Ltd.); Silopren LSR 2030, Silopren LSR 2040, Silopren LSR 2050, Silopren LSR 2060, and Silopren LSR 2070 (all trade names, available from Momentive Performance Materials Japan LLC); ELASTOSIL LR 3003/30, ELASTOSIL LR 3003/40, ELASTOSIL LR 3003/50, ELASTOSIL LR 3003/60, and ELASTOSIL LR 3003/70 (all trade names, available from Asahi Kasei Wacker Silicone Co., Ltd.).

The above primer layer can be formed by applying primer treatment agents. The primer treatment agents can be used alone or as a mixture of several commercially available primer treatment agents described below. And, if necessary, it can also be used by mixing with a catalyst, diluting solvents, modified silicones and silane coupling agents, etc.

Examples of the primer treatment agents are primer AQ-1, primer C, primer MT, primer T, primer D, primer A-10, primer R-3, and primer B-20 (all trade names, available from Shin-Etsu Chemical Co., Ltd.); Primer A, Primer B, Primer C, Primer D, SILASTIC DY39-067, SILASTIC DY39-123, DOWSIL Primer-X, and DOWSIL Primer-Y (all trade names, available from Dow-Toray Co., Ltd.); and ME21, XC9214, XP82-002, and XP81-A6361 (all trade names, available from Momentive Performance Materials Japan LLC).

As the above catalyst, the conventional one is selected from carboxylic acid metal salts, organotin compounds, alkoxytitanium compounds, organoaluminum compounds, organozirconium compounds, platinum, platinum compounds, palladium, palladium compounds, rhodium, rhodium compounds, or the like.

As the above diluting solvent, the conventional one is selected from aliphatic hydrocarbons, alicyclic hydrocarbons, ethers, esters, ketones, alcohols, or the like.

As the above modified silicone, a compound in which a part of methyl groups of PDMS (polydimethylsiloxane) is replaced by organic or substituent groups can be used. The organic and substituent groups are specifically an amino group, epoxy group, carbinol group, polyether group, mercapto group, carboxyl group, carboxylic acid group, hydrogen group, acryl group, metacryl group, phenol group, silanol group, aralkyl group, alkyl group, phenyl group, fluoro group, aliphatic acid group, aliphatic acid amide group, or the like.

As the above silane coupling agents, a material which contains both an organic group and a functional group possible to connect with an inorganic material within the molecule thereof can be used. The specific structure of the silane coupling agent is depicted as having $X_n$—$Si(OR)_{4-n}$ (n=1-3, X denotes a functional group to connect with an organic material, OR is an alkoxy group). As X, a vinyl group, epoxy group, acryl group, metacryl group, amino group, mercapto group, isocyanate group, ureido group, and styryl group, etc. are typical, but other groups are also acceptable. As the silane coupling agents in addition to monomers, oligomers and polymers are also common, including silicon compounds such as silazanes (disilazane and polysilazane) as special items.

The slidable rubber material of the present invention is produced as follows.

First of all, the rubber part-forming composition containing at least any one of the rubber component selected from the butyl rubber, halogenated butyl rubber and polychloroprene rubber, the filler, the vulcanization agent, and optionally, an additive such as alkoxysilane compounds as silane coupling agents, acid acceptors or colorants, and/or antiadhesion and viscosity regulators or processing auxiliary agents including softeners, are all kneaded with open rolls, etc.

By the way, to prepare a rubber part-forming composition, an integral blend method that all ingredients are formulated together can also be used. Alternatively, a preparing method, which comprising the preparation of surface-treated fillers by reacting fillers first with alkoxysilane compounds as a pre-treatment and then preparation by filling with those surface-treated fillers to remaining each component followed by kneading, can also be used.

As a direct surface treatment of the fillers with the alkoxysilane compounds in advance, the method, which comprises stirring an aqueous solution of silane coupling agents, i.e., alkoxysilane compounds, with a powdered filler, and then heating and drying and reacting them, can be used. By reacting and binding reactive functional groups such as a hydroxyl group on the filler surface to alkoxy groups of the alkoxysilane compounds, the alkoxysilane compounds can be set on the filler surface.

Whether it is the composition for rubber parts mixed and blended with all ingredients at once or the other composition for rubber parts using the fillers pre-treated on their surface with alkoxysilane compounds, similarly, the alkoxysilane compounds are chemically bonded to the filler surface by being vulcanized and molded, and then a rubber part in which the filler is bonded to the halogenated rubber via the alkoxysilane compound can be obtained.

Next, to the cavity of a vulcanization mold such as a dual-piece-type vulcanization mold having a male-type that forms a plunger hole with a protrusion and a female-type machined to form a cone is filled an appropriate amount of the kneaded rubber part-forming composition, and then this is subjected to heat-pressing and decoration at 165-190° C. and at 15-20 atmospheric pressure for 7-20 min, favorably 7-15 min, to be molded into a sheet. A number of gasket-shaped sheets formed into sheets are subjected to vent-pressing, and then cut into the desired gasket-shaped individual piece by using a pulling mold. This gasket-shaped piece is rinsed, if necessary. This rinsing process relies on rinsing by water and/or alkaline rinsing with aqueous sodium carbonate solution followed by acid-rinsing with aqueous sulfuric acid solution. This gasket piece is dried, if necessary.

The hardness of the gasket-shaped piece obtained above is favorably a Duro A hardness of 40 as lower-limit, more favorably 50, and is favorably a Duro A hardness of 75 as upper-limit, more favorably 70, much more favorably 65, most favorably 60 (JIS K 6253 Duro A).

To the above emulsion for the interfacial modification layer-forming composition containing amino-modified silicone compounds, whose fluid was heated to 20-80° C., favorably around 30-50° C., are immersed the pieces of gasket shape, not particularly limited, for 5 min to 6 h, favorably about 10 min to 1 h, and then, after the composition is applied to those pieces, favorably water-rinsed and dried. Although the drying condition is not particularly limited, it is desirable to dry at 120° C. or less, or air-drying by blowing high-pressure air is also fine for the molded body after water-rinsing. This surface treatment can form the interfacial modification layer on the gasket piece.

The composition for coating layers containing the solid fine particles such as silicone fine particles or silica fine particles, the addition-type and/or condensation-type silicone rubber ingredients in which the solid fine particles are dispersed, and a curing catalyst such as a platinum catalyst is prepared. Thereafter when onto the interfacial modification layer on the individual piece having a gasket-shape the above composition is applied to the desired thickness by applying with a sprayer like a spray gun, optionally heated up to cure at 80-200° C. for 5 min-2 h to form the applied coating layer, a medical gasket can be obtained as the slidable rubber material.

When the end of the plunger is pushed into the plunger hole of the above gasket, and then the plunger with gasket is inserted into a syringe barrel or injector barrel, a syringe or injector can be formed. The syringe may be the pre-filled syringe.

By the way, although an example to form directly the coating layer on the interfacial modification layer is shown here, the coating layer can also be formed as follows: the application of a primer treatment agent onto the interfacial modification layer with a sprayer like a spray gun followed by the formation of a primer layer by drying at room temperature or under heat, and finally the application of the composition for coating layers and curing similarly as described above.

EMBODIMENTS

The following is a detailed explanation of examples of the implementation of the present invention for medical gaskets made of slidable rubber materials. At first, adhesion strength was evaluated using their sheet shapes.

Example 1

The composition for rubber parts was prepared to evaluate the adhesion strength.

After stirring and mixing 100.00 parts by mass of chlorinated butyl rubber (JSR CHLOROBUTYL 1066: trade name, available from JSR Corporation) as a polymer component, 0.30 parts by mass of stearic acid (purified stearic acid 550V: trade name, available from KAO co., Ltd.), 0.30 parts by mass of zinc stearate (Zn-St (plant): trade name, available from NITTO Chemical Industry Co., Ltd.), and 5.00 parts by mass of paraffinic oil (DYANA PROCESS OIL PW-380: trade name, available from IDEMITSU KOSAN Co., Ltd.) as processing aid agents, 2.00 parts by mass of magnesium oxide (Kyowa Magu #30: trade name, available from Kyowa Chemical Industry Co., Ltd.) as an acid-acceptor, 0.30 parts by mass of carbon black (Asahi #35: trade name, available from Asahi Carbon Co., Ltd.) and 3.00 parts by mass of sulfuric acid method rutile-type titanium oxide (TIPAQUE R-630: trade name, available from Ishihara Sangyo Kaisha, Ltd.) as colorants, 60.00 mass % of talc (GH3: trade name, available from Hayashi Kasei Co., Ltd.) and 20.00 mass % of ultra-high molecular weight polyethylene (MIPELON XM-220: trade name, available from Mitsui Chemicals Inc.) as fillers, and 0.60 mass % of 3-mercaptopropyltrimethoxysilane (DOWSIL Z-6062 Silane: trade name, available from Dow-Toray Co., Ltd.) as an alkoxysilane compound with a sealed pressure kneader, to this kneaded mixture was added 0.70 parts by mass of 6-(dibutylamino)-1,3,5-triazine-2,4-dithiol (ZISNET DB: trade name, available from Sankyo Kasei Co., Ltd.) as a vulcanization agent and stirred and mixed with an open roll to obtain the composition for rubber parts.

The composition for rubber parts was cut properly in an automatic machine to fill into a cavity of a vulcanization mold with an appropriate weight and shape, and the rubber raw material was pre-molded. This pre-molded rubber raw material was put into a rubber sheet-forming mold followed by press-heating in a vulcanization-molding press-machine at 180° C. for 10 min, and, after vulcanization and molding into a sheet shape of size 50×50×2 mm, the rubber sheet was obtained.

The above rubber sheet was immersed in 0.6 weight % of an aqueous sodium carbonate solution and boiled for 90 min, thereafter immersed in 1.9 weight % of an aqueous sulfuric acid solution for 120 min at room temperature, and, after the chemical cleaning treatment, the chemically cleaning rubber sheet was prepared.

An emulsion solution was prepared by mixing 25.0 g of an amino-modified dimethylsilicone oil bearing hydroxyl groups at both terminals (DOWSIL BY16-892: trade name, available from Dow-Toray Co., Ltd.), 2.7 g of a surfactant (NIKKOL BT-9: trade name, available from NIKKO Chemicals Co., Ltd.), and 72.3 g of 0.5 weight % of an aqueous acetic acid solution followed by stirring for 10 min at 8000 rotation/min with a homo-mixer.

By using the above-prepared emulsion solution, the chemically cleaning rubber sheet was immersed in a mixture of aqueous solutions of an amino-modified dimethylsilicone oil with the final concentration of 0.05 weight % and sodium bicarbonate with the final concentration of 0.01 weight % at 40° C. for 45 min. Thereafter the rubber sheet was taken out of the liquid and, after immersion again in water, rinsed three times. The water-rinsing was performed every time by changing the water, and each time it was immersed for 1 min. And by treating by heat at 80° C. for 60 min followed by drying, the interfacial modification layer having amino-modified silicone compounds was formed to cover the chemically cleaning rubber sheet.

On the above chemically cleaning rubber sheet with an interfacial modification layer was set 50×20 mm of a PET film, and a part of the sheet was masked. Then on this was put a square frame made of PMMA (outer diameter: 50×50 mm, inner diameter: 40×40 mm, height: 2 mm), and into this frame was flowed an addition-curing type silicone rubber (KE-1950-30A/B: trade name, available from Shin-Etsu Chemical Co., Ltd., Duro 30°). Then upon grading until the surface was smooth, the whole was heated to cure in a heating oven (DKM300: trade name, available from Yamato Scientific Co., Ltd.) at 140° C. for 1 h. After curing, removal of the frame, cutting off areas where the silicone was not in contact, positioning the masking at the top, and cutting in short with 20 mm wide gave the rubber sheet for adhesion strength evaluation.

(Evaluation of Adhesion Strength)

The evaluation of adhesion strength of the above-obtained rubber sheet for adhesion strength evaluation was performed by using an instrument of a digital force gauge (HF-100: trade name, available from Japan Instrumentation System Co., Ltd.) at a tension speed of 50 mm/min with a peeling angle 180°. The results are shown in Table 1.

Example 2

In the same manner as Example 1, the chemically cleaning rubber sheet was prepared. To this sheet, after forming the interfacial modification layer, was applied a primer-blended agent, which was prepared by mixing a primer treatment agent A: primer C (trade name, available from Shin-Etsu Chemical Co., Ltd.), aluminum chelate D (trade name, available from Kawaken Fine Chemicals Co., Ltd.) and xylol (xylene WAKO special grade: trade name, available from FUJIFILM Wako Pure Chemical Corporation) in a weight ratio of 30:0.3:70 with a spray gun and dried at room temperature for 30 min to prepare the rubber sheet with a primer layer on the interfacial modification layer.

In the same manner as Example 1, the rubber sheet for adhesion strength evaluation was prepared from the rubber sheet with a primer layer on the interfacial modification layer, and the evaluation was performed similarly. The results are shown in Table 1.

Example 3

The primer treatment agent B: primer C (trade name, available from Shin-Etsu Chemical Co., Ltd.), Acrydic A-9585 (trade name, available from DIC Corporation), and xylol (xylene WAKO special grade: trade name, available from FUJIFILM Wako Pure Chemical Corporation) were mixed together in a weight ratio of 30:0.3:70 to afford a primer-blended agent. This agent was used to form the rubber sheet for adhesion strength evaluation similarly as shown in Example 2, and the evaluation was performed similarly. The results are shown in Table 1.

Example 4

The primer treatment agent C: primer C (trade name, available from Shin-Etsu Chemical Co., Ltd.), DOWSIL RSN-0805 Resin (trade name, available from Dow-Toray Co., Ltd.) and xylol (xylene WAKO special grade: trade name, available from FUJIFILM Wako Pure Chemical Corporation) were mixed together in a weight ratio of 30:0.3:70 to afford the primer-blended agent. This agent was used to form the rubber sheet for adhesion strength evaluation similarly as shown in Example 2, and the evaluation was performed similarly. The results are shown in Table 1.

Comparative Example 1

In the same manner as Example 1, the chemically cleaning rubber sheet was prepared, and without forming an interfacial modification layer, the rubber sheet for adhesion strength evaluation was prepared, and the evaluation was performed similarly. The results are shown in Table 1.

Comparative Example 2

25 g of the polyether-modified organosiloxane (KM-244F: trade name, available from Shin-Etsu Chemical Co., Ltd.), 2.7 g of a surfactant (NIKKOL BT-9: trade name, available from NIKKO Chemicals Co., Ltd.) and 72.3 g of 0.5 wt % of aqueous acetic acid solution were mixed to afford the emulsion solution. This solution was used to form the interfacial modification layer with a rubber sheet for adhesion strength evaluation similarly as shown in Example 1, and the evaluation was performed similarly. The results are shown in Table 1.

Comparative Example 3

The emulsion solution of dimethylsilicone oil (KM-742T: trade name, available from Shin-Etsu Chemical Co., Ltd.) was used to form the interfacial modification layer with a rubber sheet for adhesion strength evaluation similarly as shown in Example 1, and the evaluation was performed similarly. The results are shown in Table 1.

machine to fill into the cavity of the vulcanization mold with an appropriate weight and shape, and the rubber raw material was pre-molded. This pre-molded rubber raw material was put into the gasket-forming mold followed by press-heating in the vulcanization-molding press-machine at 180° C. for 10 min, and, after vulcanization and molding into the gasket-shape, a rubber part sheet for gaskets was obtained.

A number of the gasket-shapes formed in the above sheet were vent-pressed, and then cut into an appropriate-shaped piece using a pulling mold to afford the rubber part for gaskets.

The above rubber part for gaskets was immersed in 0.6 weight % of an aqueous sodium carbonate solution, after boiling for 90 min, and immersed again in 1.9 weight % of an aqueous sulfuric acid solution at room temperature for 120 min as a chemically cleaning treatment. Finally, the rubber part was taken out of the solution to afford the chemically cleaning gaskets An emulsion solution was prepared by mixing 25.0 g of an amino-modified dimethylsilicone oil bearing hydroxyl groups at both terminals (DOWSIL BY16-892: trade name, available from Dow-Toray Co., Ltd.), 2.7 g of a surfactant (NIKKOL BT-9: trade name, available from NIKKO Chemicals Co., Ltd.), and 72.3 g of 0.5 weight % of an aqueous acetic acid solution followed by stirring for 10 min at 8000 rotation/min with a homo-mixer.

By using the above-prepared emulsion solution, the rubber part for chemically cleaning gaskets was immersed in a mixture of aqueous solutions of amino-modified dimethylsilicone oil with the final concentration of 0.05 weight % and sodium bicarbonate with the final concentration of 0.01

TABLE 1

| | | Ex. 1 | Ex. 2 | Ex. 3 | Ex. 4 | Comp. Ex. 1 | Comp. Ex. 2 | Comp. Ex. 3 |
|---|---|---|---|---|---|---|---|---|
| Interfacial Modification Layer | DOWSIL BY 16-892 (Amino-modified) | Yes | Yes | Yes | Yes | | | |
| | KM-244F (Polyether-modified) | | | | | | Yes | |
| | KM-742T (Dimethylsilicone) | | | | | | | Yes |
| Primer Layer | Primer Treatment Agent A | | Yes | | | | | |
| | Primer Treatment Agent B | | | Yes | | | | |
| | Primer Treatment Agent C | | | | Yes | | | |
| Adhesion Strength (N) | n = 1 | 8.8 | 9.9 | 9.7 | 12.4 | 0.3 | 0.4 | 0.5 |
| | n = 2 | 11.5 | 10.4 | 12.2 | 11.3 | 0.3 | 0.3 | 0.4 |
| | n = 3 | 11. | 10.2 | 12.0 | 10.9 | 0.3 | 0.1 | 0.5 |
| | Maximum | 11.5 | 10.4 | 12.2 | 12.4 | 0.3 | 0.4 | 0.5 |
| | Average | 10.4 | 10.2 | 11.3 | 11.5 | 0.3 | 0.2 | 0.4 |

As Table 1 shows, in examples 1-4, the adhesion strength was strong and compared to comparative examples 1-3 excellent results were obtained.

Next, the evaluation was performed as a gasket for medical use.

Example 5

In the same manner as Example 1, the composition for rubber parts was prepared and cut properly in an automatic weight % at 40° C. for 45 min. Thereafter the rubber part was taken out of the liquid and, after immersion again in water, rinsed three times. The water-rinsing was performed every time by changing the water, and each time it was immersed for 1 min. By treating by heat at 80° C. for 60 min and drying the interfacial modification layer having amino-modified silicone compounds was formed to cover the rubber part.

A silicone resin (X-40-2667A: trade name, available from Shin-Etsu Chemical Co., Ltd.) was heated to cure at 105° C.

for 2 h followed by at 170° C. for 2 h in order to obtain a hardened material, and then it was crushed with a ball mill and classifying, to afford 20 weight % of silicone fine particles with an average diameter of 10 μm. A mixture of an addition-curing-type silicone rubber (KE-1950-30A/B: trade name, available from Shin-Etsu Chemical Co., Ltd., Duro A hardness 30°), 20 weight % of the silicone fine particles and xylol (xylene WAKO special grade: trade name, available from FUJIFILM Wako Pure Chemical Corporation) in a weight ratio of 8:2:90 was applied onto the rubber part for chemically cleaning gaskets that has the formed interfacial modification layer by a spray gun to form a coating film with 10 μm thickness, treated by heat at 140° C. for 60 min and cured. This gave a coating layer on the interfacial modification layer, and the desired slidable rubber material for medical use was obtained.

(Evaluation of Sliding Resistance)

The above slidable rubber material was attached to a plunger of a syringe barrel for 1 mL (inner diameter ca. φ6.35 mm) with a COP-resin outer barrel. To this syringe barrel, a plunger with a slidable rubber material was pushed 10 mm from a barrel flange, and then the syringe was installed in a fixture for measuring sliding resistance.

After the syringe was installed in a fixture, an instrument of a digital force gauge (HF-100: trade name, available from Japan Instrumentation System Co., Ltd.) was placed at the bottom of the plunger followed by pushing in 30 mm at a push speed of 100 mm/min, and then the maximum load at that time was evaluated as a sliding resistance. Furthermore, when the plunger was sucked by hand after push-in, it was checked if the plunger could escape from the slidable rubber material: i.e., 0 indicates what was not missing, and X indicates what was missing. The results are shown in Table 2.

(Evaluation of Leakage Resistance)

According to JIS T3210, the leakage evaluation was performed. The slidable rubber material was attached to the syringe barrel for 1 mL (inner diameter ca. φ6.35 mm) with a COP-resin outer barrel and 0.75 mL of water was put in the syringe. Then, after fixing it to prevent water from coming out of the barrel, pressure was applied to the plunger at 490 kPa for 10 sec. In this case, after confirmation of no drops of water from the mating part, leakage was evaluated: i.e., 0 indicates that there was no leak, and X indicates that the leak occurred. The results are shown in Table 2.

(Evaluation of Insoluble Particles)

According to The Japan Pharmacopeia Seventeenth Edition, General Test 6.97, Insoluble Fine Particles Testing Method for Injector, 1st Method of Optical Shielding Particle Measurement, the evaluation of insoluble particles was performed. The slidable rubber material and the COP-resin outer barrel for 5 mL were both rinsed with water for fine particles testing. This slidable rubber material and plunger were attached to the outer barrel, after suction of 5 mL of water for fine particles testing, and then drained into a clean container. This operation was performed 10 sets. After combining these fluids followed by allowing to stand for 2 min to remove air bubbles, a testing fluid was in hand. Then in this testing fluid the number of particles with particle sizes of 10 μm or more and 25 μm or more was respectively measured by four fractions with a particle counter for liquid (KL-06: trade name, available from RION Co., Ltd.): conditions, dilution ratio=1, suction flow=25 mL and measurement amount=5 mL. After the first fraction was discarded, an average number of particles in the testing liquid was determined from the measurement of remained three fractions, and the number of fine particles per one rubber material was calculated. The results are shown in Table 2.

Example 6

In the same manner as Example 5, the rubber parts for chemically cleaning gaskets that formed an interfacial modification layer were prepared and a mixture of an addition-curing-type silicone rubber (KE-1950-30A/B: trade name, available from Shin-Etsu Chemical Co., Ltd., Duro A hardness 30°), a silicone resin as solid fine particles (X-40-2667A: trade name, available from Shin-Etsu Chemical Co., Ltd.) was heated to cure at 105° C. for 2 h followed by at 170° C. for 2 h, after crushing with a ball mill, to afford the hardener product. A mixture of this product, 15 weight % of silicone particles with an average diameter of 2 μm obtained by classification and xylol (xylene WAKO special grade: trade name, available from FUJIFILM Wako Pure Chemical Corporation) in a weight ratio of 8.5:1.5:90 was applied to the above rubber parts by a spray gun to form the coating film with 10 μm thickness. The product was treated by heat at 140° C. for 60 min and cured to afford the slidable rubber materials. The evaluation results are shown in Table 2.

Example 7

In the same manner as Example 5, the rubber parts for chemically cleaning gaskets that formed an interfacial modification layer were prepared and a mixture of addition-curing-type silicone rubber (KE-1950-30A/B: trade name, available from Shin-Etsu Chemical Co., Ltd., Duro A hardness 30°), 5 weight % of precipitated silica as solid fine particles (VN3 (average particle diameter 10 μm): trade name, available from Tosoh-Silica Co., Ltd.), and xylol (xylene WAKO special grade: trade name, available from FUJIFILM Wako Pure Chemical Corporation) in a weight ratio of 9.5:0.5:90 was applied to the above rubber parts by a spray gun to form the coating film with 10 μm thickness. The product was treated by heat at 140° C. for 60 min and cured to afford the slidable rubber materials. The evaluation results are shown in Table 2.

Comparative Example 4

In the same manner as Example 5, the rubber parts for chemically cleaning gaskets that formed an interfacial modification layer were prepared and a mixture of addition-curing-type silicone rubber (KE-1950-30A/B: trade name, available from Shin-Etsu Chemical Co., Ltd., Duro A hardness 30°) and xylol (xylene WAKO special grade: trade name, available from FUJIFILM Wako Pure Chemical Corporation) in a weight ratio of 10:90 was applied to the above rubber parts by a spray gun to form coating films with 10 μm thickness. The product was treated by heat at 140° C. for 60 min and cured to afford the slidable rubber materials. The evaluation results are shown in Table 2.

TABLE 2

| | Material | Particle Size | Ex. 5 | Ex. 6 | Ex. 7 | Comp. Ex. 4 |
|---|---|---|---|---|---|---|
| Solid Fine Particles | Silicone Resin | 2 μm | | Yes | | |
| | | 10 μm | Yes | | | |
| | Silica | 10 μm | | | Yes | |
| Sliding Resistance (N) | | n = 1 | 5.4 | 6.4 | 6.9 | 10.3 |
| | | n = 2 | 5.2 | 6.5 | 7.0 | 11.0 |
| | | n = 3 | 5.6 | 6.3 | 6.8 | 10.1 |
| | | Maximum | 5.6 | 6.5 | 7.0 | 11.0 |
| | | Average | 5.4 | 6.4 | 6.9 | 10.5 |
| Pulling out during Suction | | Evaluation | O | O | O | X |
| Leakage Resistance | | n = 1 | O | O | O | O |
| | | n = 2 | O | O | O | O |
| | | n = 3 | O | O | O | O |
| | | Evaluation | Suitable | Suitable | Suitable | Suitable |
| Insoluble Particles | n = 1 | 10 μm | 6 | 3 | 5 | 5 |
| | | 25 μm | 0 | 0 | 0 | 0 |
| | n = 2 | 10 μm | 3 | 1 | 8 | 7 |
| | | 25 μm | 0 | 0 | 0 | 0 |
| | n = 3 | 10 μm | 3 | 0 | 3 | 5 |
| | | 25 μm | 0 | 0 | 0 | 0 |
| | Particle Average | 10 μm | 4 | 1 | 5 | 6 |
| | | 25 μm | 0 | 0 | 0 | 0 |
| | | Evaluation | Suitable | Suitable | Suitable | Suitable |

As shown in Table 2, in examples 5-7, the slidable resistance was lower than the comparative example 4 and low slidable resistance could suppress the plunger pull during suction. Furthermore, it expressed excellent leak resistance, fewer insoluble particles and excellent physical properties.

INDUSTRIAL APPLICABILITY

The slidable rubber material of the present invention can be used as follows: syringes that inject a liquid medicine into patients after inhaled it and then pushed it out, pre-filled syringes that inject a pre-sealed liquid medicine into patients by pushing it out when used or into an infusion solution, and syringes for blood drawing. In addition, this material can also be used as a variety of slidable rubber parts including medical gaskets, or the like.

The method for producing the slidable rubber material elucidated in the present invention is simple to operate using inexpensive raw materials and easy to mass-produce with good yields. In conclusion, the method is useful for producing high quality slidable rubber materials.

What is claimed is:

1. A slidable rubber material, which has an amino-modified interfacial modification layer, comprising:
    a rubber part containing a rubber component selected from the group consisting of butyl rubber, halogenated butyl rubber and polychloroprene rubber, a filler, a vulcanization agent and a vulcanizing auxiliary agent;
    an interfacial modification layer which coats the rubber part and in which an amino-modified silicone compound is incorporated and/or reacted with surface molecules of the rubber part; and
    a coating layer which coats the interfacial modification layer and contains solid fine particles, an addition-type and/or condensation-type silicone rubber in which the solid fine particles are dispersed, and a curing catalyst for the silicone rubber, and
    a thickness of the coating layer is 5-30 μm.

2. The slidable rubber material according to claim 1, wherein the amino-modified silicone compound is an amino-modified silicone oil having an amino-substituent on any one of silicone-repeating-units and/or at a terminal; or an amino-modified silicone oil having an amino-substituent on any one of silicone-repeating-units and/or at a terminal while having a hydroxyl group or a protected hydroxyl group on any one of silicone-repeating-units and/or at a terminal.

3. The slidable rubber material according to claim 1, wherein the solid fine particles are silica particles and/or silicone particles.

4. The slidable rubber material according to claim 1, wherein an average particle size of the solid fine particles is 0.1-10 μm.

5. The slidable rubber material according to claim 1, wherein a part of the solid fine particles provides with an uneven surface on the coating layer.

6. The slidable rubber material according to claim 1, wherein the coating layer neither include nor hold a silicone oil inside and on an exposed surface thereof.

7. The slidable rubber material according to claim 1, wherein the filler is silica, talc, titanium oxide, carbon black, clay and/or calcium carbonate.

8. The slidable rubber material according to claim 1, wherein the vulcanization agent is a mercaptobenzimidazole derivative and/or a triazine dithiol derivative.

9. The slidable rubber material according to claim 1, wherein the vulcanizing auxiliary agent is an organic acid zinc salt.

10. The slidable rubber material according to claim 1, wherein the rubber part includes any one selected from the group consisting of;
    an acid-acceptor selected from magnesium oxide, zinc oxide, and natural or synthetic hydrotalcite,
    an alkoxysilane compound, and
    a softening agent selected from an organic resin, and a silicone oil or a paraffin oil.

11. The slidable rubber material according to claim 1, wherein the curing catalyst is a platinum catalyst.

12. The slidable rubber material according to claim 1, wherein the coating layer is provided over the interfacial modification layer directly or through a primer layer.

13. The slidable rubber material according to claim 1, wherein the slidable rubber material is used for medical purposes.

14. The slidable rubber material according to claim 1, wherein the slidable rubber material is a gasket of a syringe or of an injector.

15. A method for producing a slidable rubber material, which has an amino-modified interfacial modification layer, comprising:
    forming an interfacial modification layer, in which an amino-modified silicone compound is incorporated and/or reacted with surface molecules of a rubber part, by applying a composition containing the amino-modified silicone compound for forming the interfacial modification layer onto the rubber part containing a rubber component selected from the group consisting of butyl rubber, halogenated butyl rubber and polychloroprene rubber, a filler, a vulcanization agent and a vulcanizing auxiliary agent, and then,
    covering the interfacial modification layer through a coating layer having a thickness of 5-30 μm by applying a composition containing solid fine particles, an addition-type and/or condensation-type silicone rubber ingredients in which the solid fine particles are dispersed, and a curing catalyst for the silicone rubber.

* * * * *